United States Patent [19]
Boehringer et al.

[11] Patent Number: 4,995,400
[45] Date of Patent: * Feb. 26, 1991

[54] PNEUMOTACH AND COMPONENTS THEREFOR

[75] Inventors: John R. Boehringer; Jay B. Nelson, both of Wynnewood; John Karpowicz, Havertown, all of Pa.

[73] Assignee: Boehringer Laboratories, Wynnewood, Pa.

[*] Notice: The portion of the term of this patent subsequent to Feb. 28, 2006 has been disclaimed.

[21] Appl. No.: 303,493

[22] Filed: Jan. 27, 1989

Related U.S. Application Data

[63] Continuation of Ser. No. 412,227, Aug. 27, 1982, Pat. No. 4,807,641.

[51] Int. Cl.$^5$ .............................................. A61B 5/08
[52] U.S. Cl. .................................................. 128/725
[58] Field of Search .................. 128/725, 724, 720; 272/99; 73/861.31

[56] References Cited

U.S. PATENT DOCUMENTS

| | | | |
|---|---|---|---|
| 2,315,756 | 4/1943 | Warner | 128/725 |
| 3,608,546 | 9/1971 | Shinn | 128/725 |
| 3,924,612 | 12/1975 | Dempster et al. | 128/725 |
| 4,051,843 | 10/1977 | Franetzki et al. | 128/720 |
| 4,807,641 | 2/1989 | Boehringer et al. | 128/725 |

Primary Examiner—Max Hindenburg
Assistant Examiner—Scott M. Getzow
Attorney, Agent, or Firm—Paul & Paul

[57] ABSTRACT

A pneumotach is provided that is effective for obtaining accurate flow measurements through a wide range of velocities by measuring substantially linear flow, and which includes a readily disposable element. The pneumotach also includes a holder adapted for readily holding the disposable element in a manner so as to be substantially free of patient contamination, and with transducer capability for detecting pressure and measuring the same at low flow rates. A combined pulmonary functioning measuring kit includes computer and read-out capabilities for selectively receiving input from either spirometer or the pneumotach. The kit is readily assembled and is self-contained.

4 Claims, 4 Drawing Sheets 4,995,400

PNEUMOTACH AND COMPONENTS THEREFOR

CROSS-REFERENCE TO RELATED APPLICATIONS

This application is a continuation of application Ser. No. 412,227 filed Aug. 27, 1982, now U.S. Pat. No. 4,807,641 dated Feb. 28, 1989.

BACKGROUND OF THE INVENTION

Pneumotachs, or pneumotachographs, as they are sometimes called, have long been known in the art. They are primarily flow-sensing devices, whose output is in the form of a pressure signal proportional to the rate of air flow. Prior art devices have generally involved keeping pressure taps of air flow at different locations along a tube, with the pressure differential between the taps used as an indication of flow measurement. However, in such prior art devices, the change in pressure is a function of the square of the velocity of flow. When the device is used to measure breathing, especially in the instances where pulmonary problems are present, the flows can vary from very low flow rates to very high flow rates, and especially covering ranges of, for example 250 to 1. Once these flow velocities are squared, the ratio becomes 62,500 to 1, thereby introducing inaccuracies.

It is also known that it is desirable to measure laminar flow, as distinguished from turbulent flow, because the pressure measurement becomes a linear, not a second-degree function. However, in many devices seeking to measure laminar flow, tubes or the like are inserted into the flow tube, leading to additional inaccuracies caused by moisture, phlegm from coughing, or similar sources, which causes condensation and blockage, and in any event produces erratic measurements.

Additionally, while both visually-read spirometric measurements and visually-read pneumotach measurements have been known, it is not believed that these measurements have heretofore been combined in a readily accessible kit, in accordance with the present invention.

SUMMARY OF THE INVENTION

The present invention resides in providing a disposable flow tube for a pneumotach, in providing a novel pneumotach, and in providing a pulmonary flow measurement kit for readout of both spirometric and pneumotachographic parameters.

Accordingly, it is a primary object of this invention to provide a novel pneumotach.

It is a further object of this invention to provide a pneumotach with a disposable flow tube.

It is another object of this invention to provide a novel pneumotach, in which a handle may readily grasp a non-reusable flow tube, and connect to the flow tube so as to allow conduit communication therewith, and with a transducer for communicating with the interior of the flow tube through the conduit.

It is another object of this invention to provide a convenient pulmonary measuring device comprising a kit capable of both spirometric and pneumotachographic measurements.

Other objects of the invention reside in providing appropriate circuitry for facilitating read-out of spirometric and pneumotachographic measurements.

BRIEF DESCRIPTION OF THE DRAWING FIGURES

DETAILED DESCRIPTIONS OF THE PREFERRED EMBODIMENTS

In the field of pulmonary function measurements, there is a need for an inexpensive, portable apparatus with sufficient accuracy to meet the standard established by the American Thoracic Society, The American College of Chest Physicians, and other organizations.

Previous instruments designed to meet specifications established by these organizations have been handicapped by the use of an orifice and flow transducer which, in order to meet accuracy specifications for pulmonary testing, have been very expensive. Other devices compromise quality or function in favor of cost. The present invention is addressed to providing a truly portable multi-function system adaptable for both clinical and screening functions, at a modest cost.

It is a goal of the system provided herein, to provide pick-off of either the electrical or optical type of data from a turbine spirometer, or to provide a pressure pick-off from a porous laminar flow transducer or pneumotach which generates an analog voltage, and with the analog voltage being converted to a digital signal, to be fed to and read from the same pulmonary computer that is utilized with the spirometer.

Accordingly, it is a goal to combine a spirometer for clinical circuit monitoring with a pneumotach for screening purposes, and to use the same computer, thereby achieving economies of manufacture.

With respect to clinical uses such as operating room use or intensive care use of the system, it is desired to eliminate calibration trouble due to gas composition changes (the so-called nitrous oxide), or trouble from water condensation. The present system therefore uses a separate, sealed, electrooptical spirometer system of the type set forth in U.S. Pat. No. 4,182,175. The present system is particularly usable with screening functions for detecting pulmonary problems, most particularly when used with a dynamic brake that will substantially immediately stop turbine rotation as breathing stops, thereby eliminating coast problems with the spirometer. Combining a dynamic brake with a sealed spirometer system also eliminates water problems and gas density viscosity problems. By using a pneumotach having a disposable element with a reusable handle as set forth herein, there is provided an inexpensive but effective way to eliminate water build-up in laminar flow elements. Additionally, the contaminated item, namely the flow tube, is readily disposable, but the handle comprises a seal for communication with the flow tube, and is non-disposable, but reusable.

Figure 1:
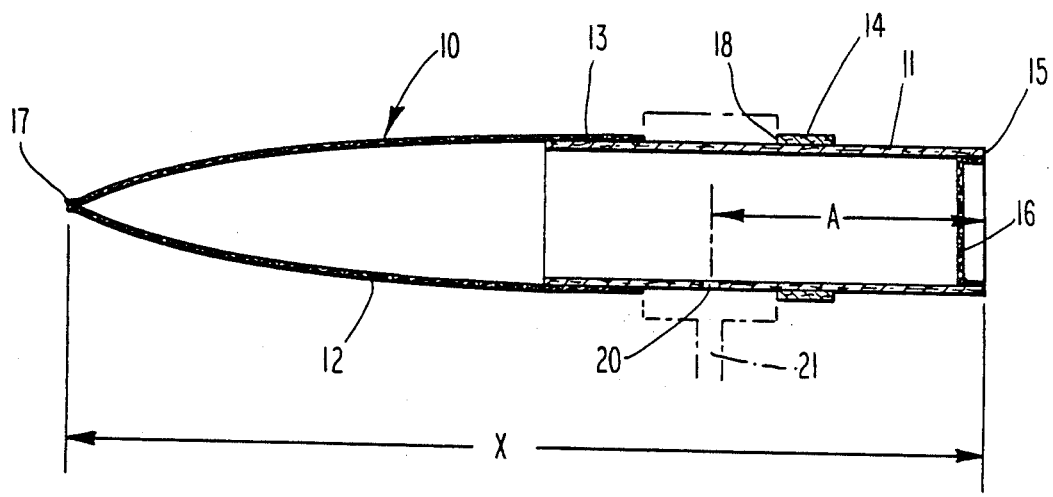
FIG. 1 is a longitudinal sectional view, taken through a disposable flow tube for a pneumotach in accordance with this invention, with a portion of the flow tube holder being shown in phantom, for purposes of illustration.

With specific reference to FIG. 1, there is provided a flow tube generally designated by the numeral 10 comprising essentially a cylindrical, generally non-porous portion 11 having a generally porous portion 12 connected thereto over the left-most end of the non-porous portion 11 as shown in FIG. 1, at 13.

The non-porous portion 11 may be constructed of paper board or the like, with a thermoplastic film, or the like, thereon, or may be of substantially rigid plastic construction, if desired. The porous portion 12 will preferably be constructed of a non-woven heat sealable filter paper, comprising many wraps or windings, until it forms a cylindrical configuration having substantial body thereto. For purposes of convenience the portion 11 may be discussed herein as being the cardboard portion, and the portion 12 as being the porous or filter portion. A locating ring 14 is disposed about the circumference of the cylinder 11, and is secured thereto by heat sealing, adhesive or the like, some distance from the mouthpiece end 15 of the tube. A porous screen 16 is disposed at the rearmost end of the tube as illustrated in FIG. 1, which is the end of the tube most proximal to the patients mouth, to smooth out flow "jetting", and to screen out foreign matter.

The left-most end of the filter portion 12 is heatsealed at 17, thereby flattening out that end of the otherwise cylindrical tubular configuration for the filter portion 12, into a pillow-end-like configuration, and which serves to prevent back leakage. The locating ring 14 is disposed with its end 18 at a precise location from the inlet end 15 of the tube, which location is also precisely coordinated with a pressure tap opening through the wall of the tube portion 11 transversely disposed as illustrated, which opening 20 is a precise distance A from the end 15 as shown, to locate the pressure tap opening at a sufficient distance away from the point of flow entry so as to eliminate "jetting" effects and to encourage the squared factor flow to remain insignificant in taking off the pressure measurement.

The left of the tube 10, designated by the dimension "X" in FIG. 1, is likewise coordinated with the spacing A, so as to maximize the linear area of the flow through the tube 10.

The pressure tap opening 20 is made to be absolutely free of intrusion of portions of the cylindrical wall 11 into the interior of the tube 11, to eliminate adverse effects on the linearity of the measurement obtained by the transducer reacting to pressure presented to the transducer through the opening 20. It is believed that, by so constructing the opening 20, the result is a subtractive term, in the equation for the pressure, the subtractive term being a function of the square of the velocity of the flow. This subtractive term counteracts an additive term that is also a function of the square of the velocity of flow. The additive term that is a function of the square of the velocity of flow, and which needs counteracting, is, in turn, related to the diameter of the tube, the porosity of the element, the ratio of mouthpiece inner diameter to porous element inner diameter, and the area of the porous element.

The above may be restated symbolically as follows. It is believed that the pressure P is related to the flow velocity V as follows:

$$P = K_1 + K_2V + K_3V^2 - K_4V^2$$

where the Ks are constants. The $K_4V^2$ term is the subtractive term described above, which counteracts the effect of the $K_3V^2$ term.

Figure 2:
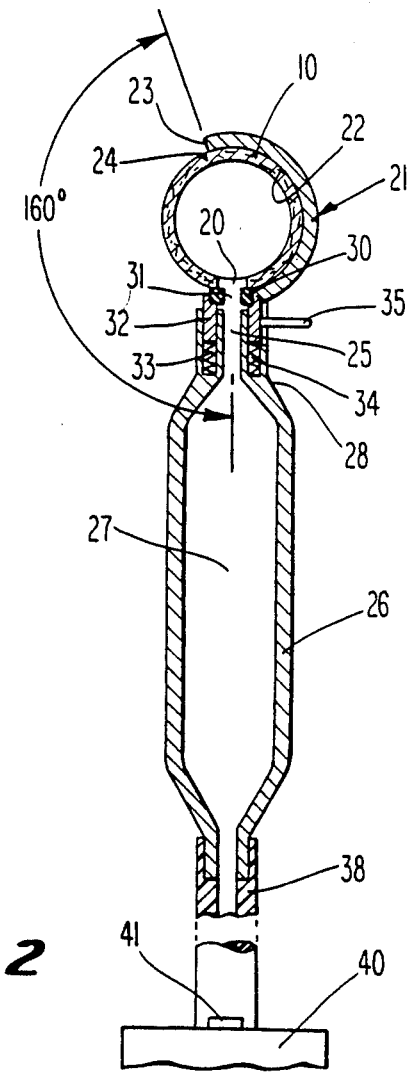
FIG. 2 is a longitudinal sectional view taken through the flow tube holder of this invention, with the flow tube itself being illustrated in transverse cross-section, and wherein the holder communicates internally to a pressure pick-up transducer at its lower end.

It will be seen that a holder 21 therefore may engage the tube 10, by being applied over its side, or in transverse approach, as is viewed in FIGS. 1 and 2, and need not be slid over the mouthpiece end 15, or opposite end 17 of the disposable tube 10. The holder 21 will be seen to engage, in FIG. 2, the tube 10, through an arc of about 200°, leaving a non-engaged arc of about 160°. The holder 21 thus has a concave interior 22 that terminates at the outer end at 23. The tube 10 will be oriented against the concave face 22, such that a scribe line 24 is lined up with the end 23, to assure that the opening 20 is properly aligned with handle 26 of the holder 21. The handle 26 has a hollow interior at 27, and an upper neck portion 28. Seated at the upper end of the neck portion 28, is a gasket or seating ring 30, of rubber or similar material, having a communicating hole 31 therethrough. The seating ring 30 is carried on a slidable sleeve 32 that is movable upwardly and downwardly toward the tube 10 and away therefrom, against the compressive force provided by compressive spring means 33, disposed in blind openings 34 in the upper end 28 of the handle 26. The sleeve 32 is provided with a tang or manually graspable portion 35 that may be engaged by the finger of a user and pulled downwardly as viewed in FIG. 2, to release tube 10, or, in the alternative, once the tube 10 is properly seated within the surface 22 of the handle 26 and oriented such that the scribe line 24 on the tube is lined up with the end 23 of the handle, and with the opening 20 lined up with the opening into the interior 27 of the handle, due to the holder 21 being disposed against the surface 18 of the ring 14, the tang 35 may be allowed to move upwardly, such that the sealing rubber or like ring 30 surrounds the hole 20 and clampingly engages the holder 26 against the tube 10.

At the lower end of the handle 26, a tube 38 of flexible plastic, or rubber, or other material, is provided, illustrated in broken form, for reasons of space saving, to communicate with a pneumotach transducer box, in which a pressure transducer 41 is located, to be exposed to the pressure delivered from inside the tube 10 through the hole 20, and against the transducer, whereby the pressure transducer 41 may react to the flow by creating a pressure- responsive electrical signal.

Figure 1A:
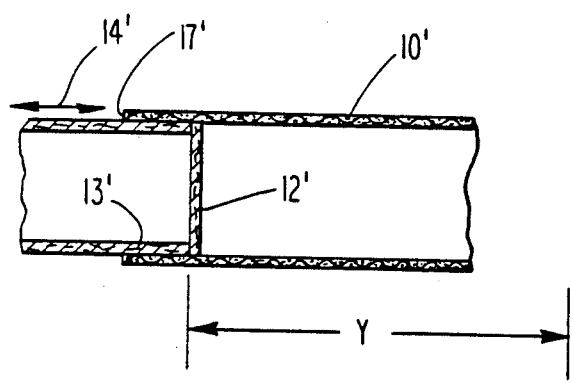
FIG. 1a is a fragmentary illustration of one form of an end of the flow tube for the pneumotach for this invention that differs from the embodiment of FIG. 1 insofar as the end of the flow tube is concerned, and in which, in FIG. 1a, the end of the flow tube remote from the user's mouth is adjustably positionable.

With particular reference now to FIG. 1a, it will be seen that the left-most end of the tube 10' is constructed such that the left-most end 17' is provided with a plug 12', that is disc-like, if viewed in transverse section, having connected thereto a sleeve-like portion 13', such that the portion 12' and 13' comprise a separate element movably positionable at different locations inside the tube 10', in the direction of the double headed arrow 14', for instances in which specific calibration of the length Y of the tube 10' is desired.

It will also be noted that the gasket or seal 30, in order to conform precisely to the exterior configuration of the tube 10 at the location of the hole 20, will generally be of concave construction when viewed from above in FIG. 2. The upper surface of the sealing gasket 30 may have various labyrinthine designs on its surface, to assure against leakage. It will be noted that by the use of a holder having an upper portion as described above, the holder may be slipped onto and off of the tube, without contamination of either end of the tube from breath of the user. In the alternative, not illustrated, the upper end of the holder could be divided into two halves, clampable over the disposable tube.

It will thus be seen that, the holder 26 may readily be provided as a re-usable member, with the tube 10 constructed as a relatively inexpensive, disposable, and non-reusable member.

Figure 3:
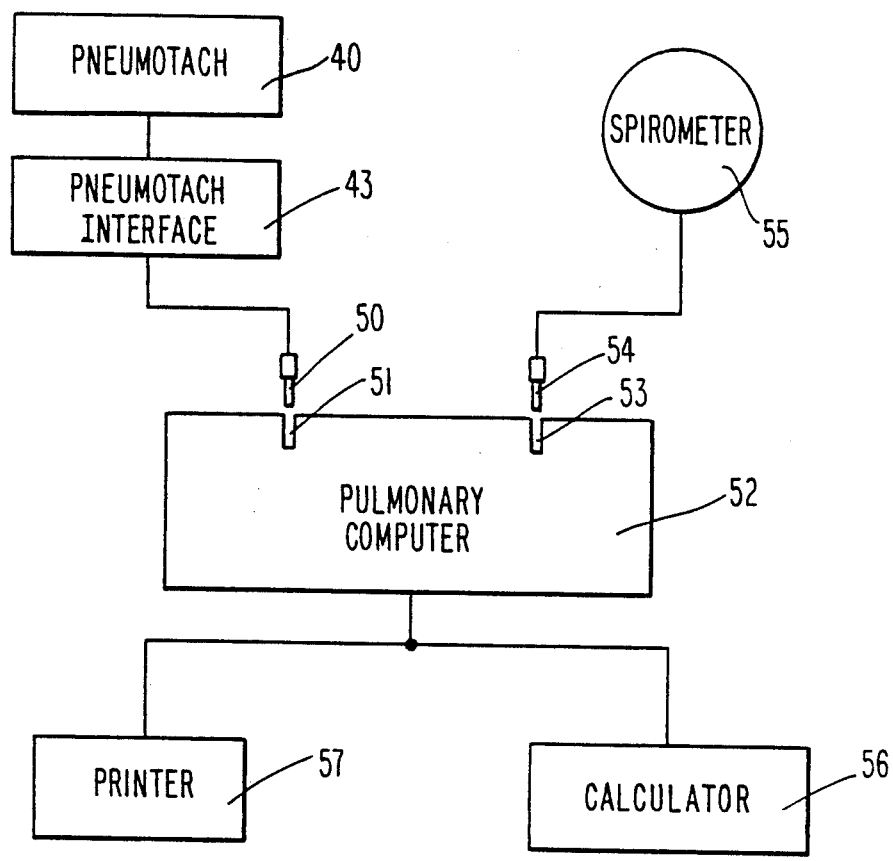
FIG. 3 is a block diagram of the various components of the system of this invention that comprise the kit.

With particular reference to FIG. 3, the interconnection of the various basic components of the present invention will be understood. The pneumotach 40 is connected through a pneumotach interface 43, by means of a suitable connection means such as the male-female type connector 50, 51 illustrated, to connect to the pulmonary computer. The pulmonary computer 52 (which comprises a microprocessor and associated components) likewise has a female connection portion 53 for receiving a male connection 54 from the spirometer 55.

It will be understood that the spirometer 55, as aforesaid, can be constructed in accordance with the structure and to accomplish the functions set forth in U.S. Pat. No. 4,182,175, or in U.S. patent application Ser. No. filed on even date herewith and entitled "Dynamic Braked Spirometer," by John R. Boehringer and C. Harrison Williams, Attorney File No. 122-82, the complete disclosure of which is herein incorporated by reference, to be part of this application. The calculator 56 (which has its own separate power supply) is designed to work with a printer or other read-out instrument 57, to print out the desired pulmonary measurements obtained by means of the pneumotach and/or spirometer. Generally, the pulmonary computer 52 will be rechargeable, battery operated, and will include a microprocessor with all of the necessary software. The primary supply in calculator 56 will contain battery or 110 volt converters, and suitable card reading and timing modules and will preferably contain a visible light display of information. The printer 57 will preferably be a high speed printer having suitable graphics capability for trend recording readout printed on paper and will contain both battery and 110 volt conversion apparatus.

Figure 4:
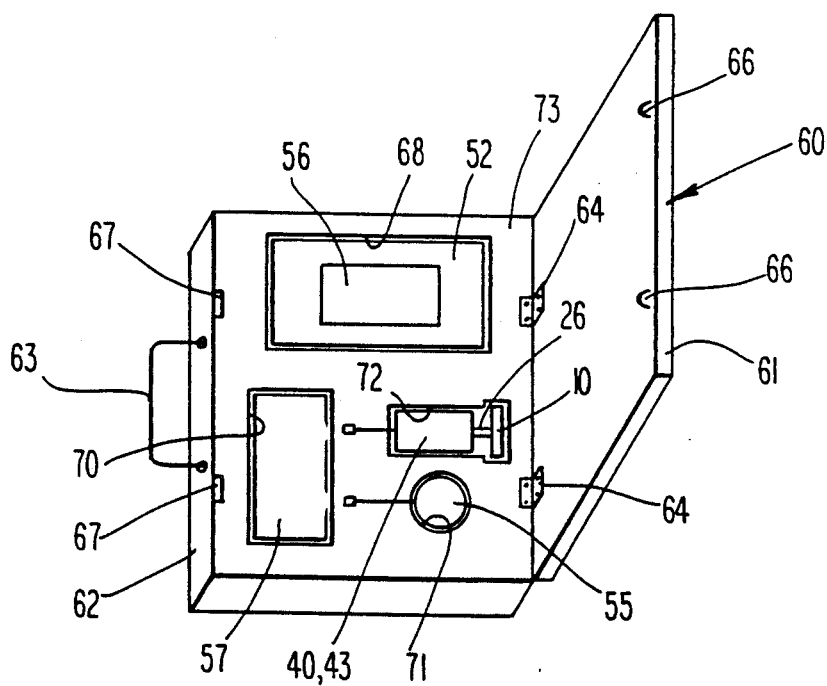
FIG. 4 is a schematic perspective view of a packaged, but open kit, in accordance with this invention.

With specific reference to FIG. 4, the readily assembled kit for the various devices illustrated in FIG. 3, is shown with the devices illustrated in attache case arrangement within a case 60. The case 60 includes a lid portion 61 a base portion 62, a handle 63 with hinges 64 and 65 for the connection of the lid portion 61 to the base portion 62, and with suitable clasp portions 66 and 67. Suitable recesses 68, 70, 71 and 72 are provided in a styrofoam or like bed or block 73, for conveniently housing the various components, 10, 52, 26, 40, 43, 57, 52 and 56 of the kit, in accordance with the present invention.

It will be noted that the pulmonary computer 52 processes the data from the pneumotach or spirometer and provides calibration corrections to the flow data, which are then stored in memory and/or processed for computation into formats for printing out.

Figure 5:
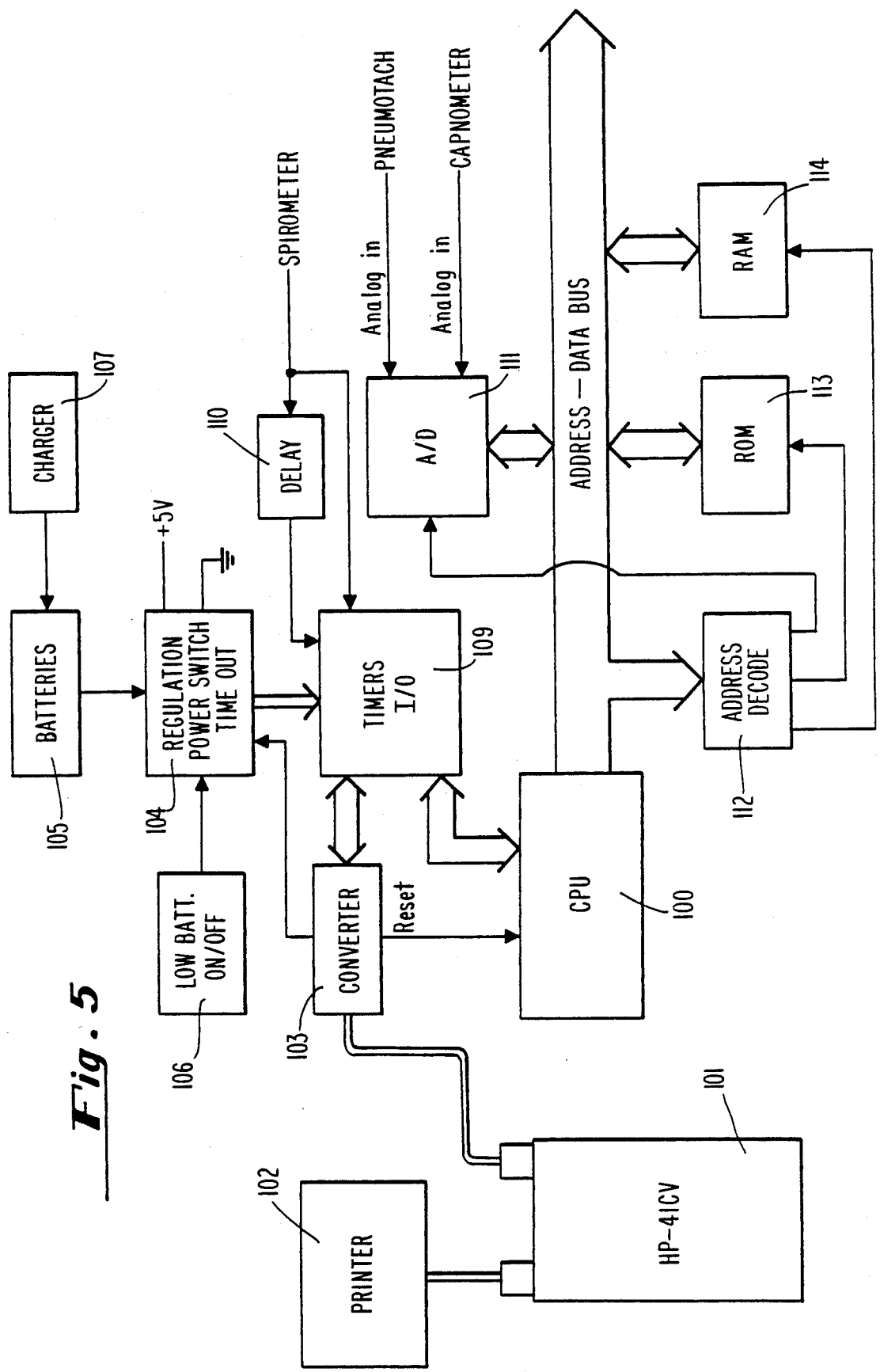
FIG. 5 is a block diagram in greater detail of the various components of the pulmonary measuring system of the present invention.

FIG. 5 is a schematic block diagram of the various components of the measuring system, showing in more detail the computer and calculator and their associated components. In FIG. 5, all of the blocks except 101 and 102 constitute the contents of block 52 in FIG. 3. The heart of the system is central processing unit (CPU) 100, which can be a microprocessor which allows the system to be operated on batteries, and to be portable. Calculator 101 is used to control the microprocessor. In the embodiment shown, the calculator is a Hewlett-Packard HP-41CV. The CPU 100 is essentially a slave to the calculator 101. When a particular key on the calculator is pressed, a signal is sent to the computer, causing the execution of a particular function. Thus, commands originate from calculator 101, and semi-processed transducer data are transferred from the computer back to the calculator for further processing, and output via printer 102.

When the system has not been used for a full minute, the computer will turn itself off, preventing excessive or accidental drain of the batteries.

Converter 103 is used to deliver all commands from the calculator to the microprocessor. For example, when a key on the calculator representing the "power up" instruction is depressed, a converter "wake-up" line is activated, which generates a pulse in power switching circuit 104. Power from the battery pack 105 is then regulated to supply the system with operating voltage. Circuit 106 provides indicator means (preferably LEDs) to inform the user that the power is on, and also to warn the user whenever the battery voltage is too low. Battery charger 107 is provided to recharge the batteries as needed.

When operation of the system is initiated, the converter 103 automatically resets the central processing unit 100, and the CPU then awaits further instructions. Further instructions from the calculator 101 come in the form of single ASCII coded letters, which are passed through to the CPU 100 via I/O port 109. Each instruction causes the CPU to jump to the appropriate program location, and a data acquisition routine is performed. Data enters the system from at least two separate sources, as shown. First, digital data, such as from a turbine spirometer, can enter the system through I/O port 109. In the case of a spirometer which is used in conjunction with a capnometer, a delay circuit 110 may be used to cancel the effect of capnometer delay. The delay circuit 110 can be a shift register, of known design. Second, data can enter the system in analog form from a pneumotach, or from a capnometer. In the latter cases, an analog signal enters the analog-to- digital (A/D) converter 111, where the signal is converted to digital form.

Data upon which the computer will operate is selected by the address decoder 112, which selects data from either ROM 113, RAM 114, or the analog-to-digital converter 111. In the preferred embodiment, the ROM 113 contains 6K of memory, partitioned as 4K of program memory and 2K of a look-up table for linearization of pneumotach data. In the preferred embodiment, the RAM contains 2K, which is used for temporary storage of data for output or internal program use.

Timing of pulses, waveform generation, and event counting are accomplished by timers, of known design, in the I/O port 109. Once a routine is completed, data are transferred from the CPU 100 back through converter 103, and to the calculator 101. From there, the data are manipulated, placed in proper format, and, if desired, output to the printer 102.

Figure 6:
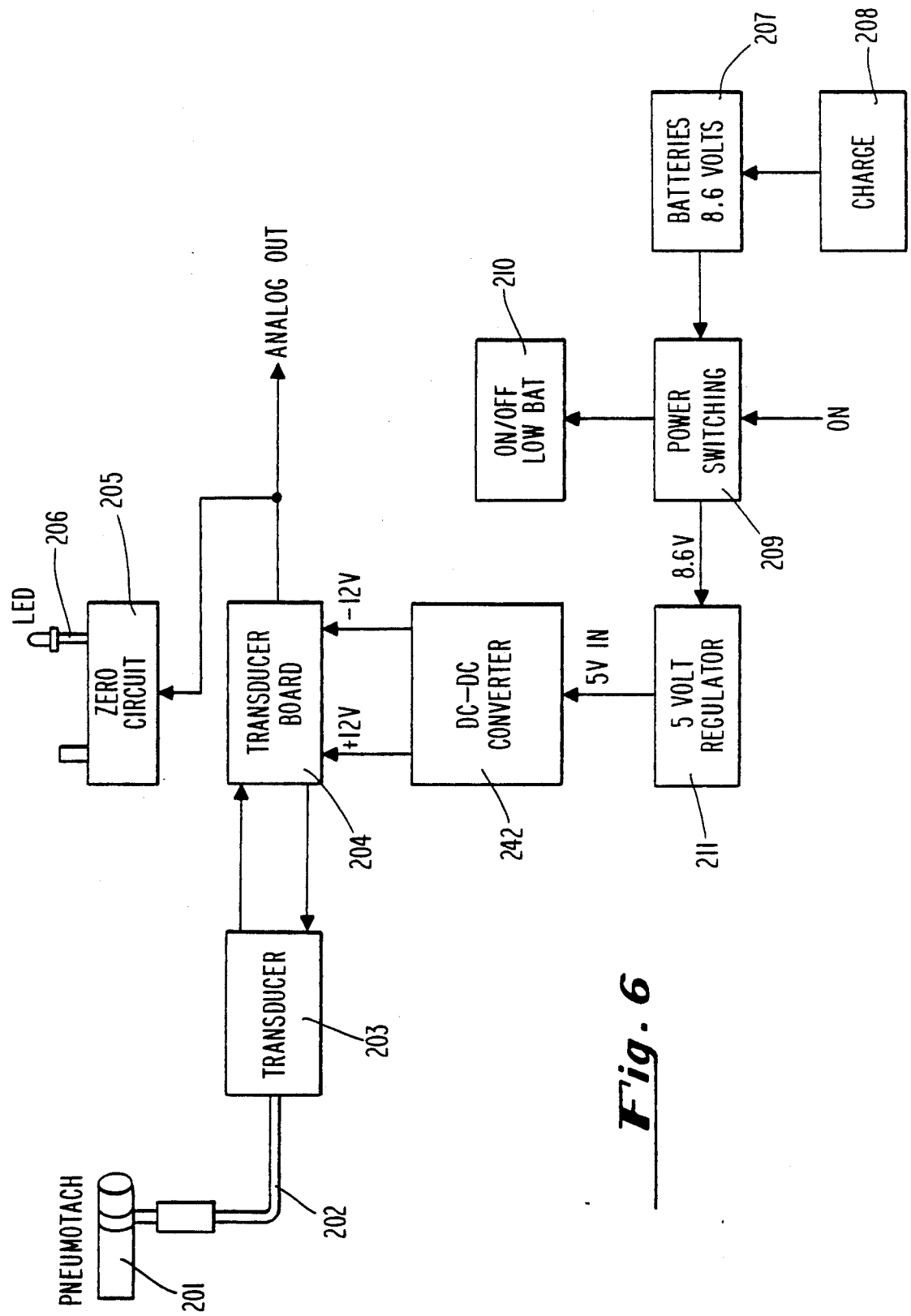
FIG. 6 is a block diagram of the transducer hook-up for the pneumotach of the present invention.

FIG. 6 is a block diagram, showing the pneumotach transducer circuit. This circuit converts a pneumotach pressure signal, which is linearly proportional to flow, to an analog voltage. The analog voltage may be used to drive oscilloscopes or automatic data plotters. In FIG. 6, there is shown pneumotach 201 which provides a back pressure linearly proportional to the flow, which is sent by a small-diameter plastic tube 202 to the transducer 203. The transducer 203 is excited by the transducer board 204, and produces an analog voltage whose span and zero point may be adjusted by trim potentiometers on the board 204. The aim in calibration is to obtain a zero signal at a zero flow. Since all analog circuits are subject to drift with time, temperature and physical shock, the zero circuit provides a zero voltage band on the order of plus or minus 5 millivolts during which span an LED is lit. If the absolute value of the voltage exceeds 5 millivolts, the LED goes out, notifying the user that the zero setting needs to be readjusted. The zero circuit is represented by reference numeral 205, and the LED is shown as 206.

The circuit in FIG. 6 is also provided with rechargeable batteries 207, and battery charger 208. Power switching unit 209 is controlled by an on/off signal from a pulmonary computer. The power switching unit also controls the circuit 210 which is an indicator that the battery voltage is too low. The signal from the power switching means 209 is fed to a voltage regulator 211 and converter 212, which increases the voltage from 5 to 12 volts.

It is seen that the objects of the invention are fulfilled by the above disclosure. Many modifications are possible. The specific embodiments shown can be constructed using various circuit elements which are readily available. It is understood that the following claims are not limited by the specific circuits chosen, but are to be deemed to include such modifications as would be apparent to those of ordinary skill in the art.

What is claimed is:

1. A pneumotach flow tube with a mouthpiece end and an opposite end, with at least said mouthpiece end being of generally cylindrical construction, said opposite end being at least substantially closed against the passage of exhaled air therethrough, said flow tube having a substantially non-porous mouthpiece portion and a substantially porous portion between the non-porous portion and the closed end, a transverse pressure tap opening through the cylindrical wall of said substantially non-porous portion, said opposite end and said pressure tap opening each being located so spaced from the mouthpiece end and the porosity of the porous flow tube portion being so sized, to be sufficient to produce substantially laminar flow in the tube and to permit substantially linear flow pressure measurements through the tap opening at the location of said pressure tap opening.

2. A flow tube as defined claim 1, including first locator means for locating a tube holder thereagainst; said first locator means comprising projection means on the periphery of said tube, spaced longitudinally along said tube from said pressure tap opening, and with second locator means disposed on the exterior of said tube for locating the orientation of the pressure tap opening relative to a tube holder.

3. The flow tube of claim 1, with said opposite end being generally flat and pillow-ended, and sealed closed.

4. A pneumotach comprising a flow tube as defined in claim 1 and including pressure transducer means for producing a pressure-responsive electrical signal, said pressure transducer means connected to said pressure tap opening by means of a conduit element and located outside of said flow tube.

* * * * *